(12) United States Patent
Trollsas et al.

(10) Patent No.: US 9,393,325 B2
(45) Date of Patent: Jul. 19, 2016

(54) BIOABSORBABLE CO-FILLER FOR CEREBROVASCULAR ANEURYSMS

(71) Applicants: Mikael Trollsas, San Jose, CA (US); Michael Huy Ngo, San Jose, CA (US)

(72) Inventors: Mikael Trollsas, San Jose, CA (US); Michael Huy Ngo, San Jose, CA (US)

(73) Assignee: Abbott Cardiovascular Systems Inc., Santa Clara, CA (US)

(*) Notice: Subject to any disclaimer, the term of this patent is extended or adjusted under 35 U.S.C. 154(b) by 104 days.

(21) Appl. No.: 14/057,961

(22) Filed: Oct. 18, 2013

(65) Prior Publication Data

US 2014/0046361 A1 Feb. 13, 2014

Related U.S. Application Data

(63) Continuation of application No. 13/282,344, filed on Oct. 26, 2011, now abandoned.

(51) Int. Cl.
*A61K 49/00* (2006.01)
*A61K 49/04* (2006.01)
*A61B 17/12* (2006.01)

(52) U.S. Cl.
CPC ....... *A61K 49/0054* (2013.01); *A61B 17/12145* (2013.01); *A61K 49/0409* (2013.01); *A61K 49/0438* (2013.01); *A61K 49/0457* (2013.01)

(58) Field of Classification Search
None
See application file for complete search history.

(56) References Cited

U.S. PATENT DOCUMENTS

| | | | |
|---|---|---|---|
| 5,356,883 A | 10/1994 | Kuo et al. | |
| 5,368,840 A | 11/1994 | Unger | |
| 5,502,081 A | 3/1996 | Kuo et al. | |
| 5,681,825 A | 10/1997 | Lindqvist et al. | |
| 6,013,679 A | 1/2000 | Kuo et al. | |
| 6,056,970 A | 5/2000 | Greenwalt et al. | |
| 6,086,597 A | 7/2000 | Fergeus et al. | |
| 6,096,021 A * | 8/2000 | Helm et al. | 604/509 |
| 6,271,216 B1 | 8/2001 | Mello et al. | |
| 6,537,979 B1 | 3/2003 | Kuo et al. | |
| 6,548,081 B2 | 4/2003 | Sadozai et al. | |
| 6,620,927 B2 | 9/2003 | Bulpitt et al. | |
| 6,884,788 B2 | 4/2005 | Bulpitt et al. | |
| 7,611,542 B2 | 11/2009 | Bourne et al. | |
| 7,829,118 B1 | 11/2010 | Gravett et al. | |
| 8,038,991 B1 | 10/2011 | Stankus et al. | |
| 2005/0149173 A1* | 7/2005 | Hunter et al. | 623/1.42 |
| 2009/0155314 A1 | 6/2009 | Tezel et al. | |

OTHER PUBLICATIONS

Shi, Changbin et al., "Genomics of Human Intracranial Aneurysm Wall", Stroke, stroke.ahajournals.org on Jun. 29, 2010, (2009), pp. 1252-1261.
Safriel et al., "Gadolinium Use in Spine Procedures for Patients With Allergy to Iodinated Contrast—Experience of 127 Procedures", AJNR am J Neuroradiol, Jun.-Jul. 2006; 27(6): abstract).
Blood Viscosity (http://en.wikipedia.org/wiki/Blood_viscosity (downloaded May 20, 2013).
Iron Oxide (http://en.wikipedia.org/wiki/Iron (II,III)_oxide (retrieved on Feb. 23, 2013).
Hyal-Joint (http://www.hyal-joint.com/Dr._Theo_responds/V3-Hyaluronic-acid.html(Sep. 30, 2010).

* cited by examiner

*Primary Examiner* — Jake Vu
(74) *Attorney, Agent, or Firm* — Randy Shen; Blakely, Sokoloff, Taylor & Zafman LLP

(57) ABSTRACT

Materials and methods for delivering materials for filling aneurysms in which the materials comprise a glycosaminoglycan and optionally, contrast media and physiological buffers and in which delivery methods include percutaneous delivery with a balloon catheter or a needle catheter.

14 Claims, No Drawings

BIOABSORBABLE CO-FILLER FOR CEREBROVASCULAR ANEURYSMS

This application is a continuation of co-pending U.S. application Ser. No. 13/282,344, filed Oct. 26, 2011.

BACKGROUND

In many cases, aneurysms form in the vessel walls of an organism. If such an aneurysm were to rupture, the organism would be in danger of severely bleeding from the rupture site. Depending on the location of the aneurysm, its rupture could lead to stroke. And if large enough, the aneurysm's rupture could even lead to exsanguination.

The extreme risks associated with aneurysms call for their treatment. Typical treatments of un-ruptured aneurysms include surgically removing them in situations where such removal is possible. Another treatment centers on filling an aneurysm sack with coils of various materials, which may decrease the pressure in the sack. In some cases, the danger from the aneurysm decreases when the pressure in the sack falls. To reduce the pressure in the sack, it is important to fill the sack well, and then slowly allow the sack to fill up with scarring or other extracellular matrix material. A practitioner could orchestrate slow filling followed by scarring or the migration of other matrix material using coils with bioabsorbable, pro-inflammatory coatings. Alternatively, changes in the hemodynamics cause by filling the aneurysm promote the formation of thrombus inside the aneurysm sack, which also lowers aneurysm pressure.

In many cases, filling treatment results in an aneurysm permanently filled with foreign material. This treatment may lower the pressure and restore normal hemodynamics near the aneurysm. But it also interferes with the aneurysm's complete healing.

What is needed is a way to temporarily fill the aneurysm in a controllable manner such that endogenous compounds could later gradually replace the filling material.

SUMMARY

As in one inventive embodiment, one useful filling material is a composition that comprises a glycosaminoglycan or a mucopolysaccharide. In some embodiments, this composition is augmented with a physiological buffer, with a contrast media or with both.

Additionally, some embodiments are formed in-situ, inside of the aneurysm sack and may additionally comprise avian protein, blood protein components, blood protein decomposition products, blood cells, blood cell decomposition products, other endogenous compounds, or coil decomposition products.

In some embodiments, the filling material is prepared as a hydrogel.

In some embodiments, the filling material is prepared so that it slowly migrates out of the aneurysm or is broken down within the aneurysm and replaced by endogenous compounds over a 7-90 day period; 14-70 day period; or 21-60 day period.

Some embodiments are directed at methods for treating aneurysms. For example, in one embodiment the method of treating an aneurysm comprises delivering a glycosaminoglycan or a mucopolysaccharide to the aneurysm or into an aneurysm. Moreover, various embodiments in which an aneurysm is treated by delivering a filling material as described in this document, to the aneurysm or into the aneurysm. A variation of these embodiments includes delivering a metallic or polymeric coil to the aneurysm before, during, or after delivery of the filling material or delivery of a glycosaminoglycan or a mucopolysaccharide.

Some embodiments use direct surgery or hypodermic needle delivery directly to the aneurysm. Other embodiments use balloon or needle catheters to deliver the filling material to the aneurysm percutaneously.

DETAILED DESCRIPTION

The following description of several embodiments describes non-limiting examples that further illustrate the invention. All titles of sections contained herein, including those appearing above, are not to be construed as limitations on the invention, but rather they are provided to structure the illustrative description of the invention that is provided by the specification.

Unless defined otherwise, all technical and scientific terms used in this document mean what one skilled in the art to which the disclosed invention pertains commonly understands them to mean. Singular forms—a, an, and the—include plural referents unless the context clearly indicates otherwise. Thus, for example, reference to "fluid" refers to one or more fluids, such as two or more fluids, three or more fluids, etc. When an aspect is said to include a list of components, the list is representative. If the component choice is specifically limited to the list, the disclosure will say so. Moreover, listing components acknowledges that embodiments exist for each of the components and any combination of the components—including combinations that specifically exclude any one or any combination of the listed components. For example, "component A is chosen from A, B, or C" discloses embodiments with A, B, C, AB, AC, BC, and ABC. It also discloses (AB but not C), (AC but not B), and (BC but not A) as embodiments, for example. Combinations that one of ordinary skill in the art knows to be incompatible with each other or with the components' function in the invention are excluded from the invention, in some embodiments.

In some embodiments, treatment methods include delivering a material to the aneurysm. So that the physician can monitor the degree of filling of the aneurysm, the material mixture may contain a contrast medium, which, for example fluoroscopy, could reveal during the treatment. The exact mechanics of delivering a material to the aneurysm depends on which type of aneurysm afflicts the patient.

Some aneurysms consist of larger regions of weakened vessel wall that may bulge from the normal vessel walls, pushed out by the blood pressure within the vessel. Other aneurysms consist of a weakening of a smaller region of the vessel wall that then balloons out from the vessel wall again pushed out by blood pressure within the vessel. These aneurysm types serve as the ends of a continuum that encompasses most aneurysms.

A difference between these two types of aneurysms is in their ability to contain a treatment agent. For example, an aneurysm with more of a balloon-like structure may be able to accept and hold a material that blood flow would wash away from a less balloon-like aneurysm or an aneurysm that simply bulges from a larger region of vessel wall. Thus, sometimes a practitioner treats aneurysm with a coil of polymeric or metallic wire such as a coil of platinum wire before introducing a "filling" material. In some embodiments, treatment comprises delivering the material to the aneurysm before, after, or during the delivery of the coil.

Regardless of the type of aneurysm and regardless of whether using a coil promotes retaining a filling material at the aneurysm site, practitioners may choose to treat the aneurysm with a filling material and either use or omit a coil at their discretion. All instances of treating an aneurysm with the filling material described in this document (with or without a coil) are within the scope of the invention.

In some embodiments, the filling material comprises a glycosaminoglycan or a mucopolysaccharide. One advantage of using a glycosaminoglycan or a mucopolysaccharide is that, over time, these materials can be replaced by compounds that are endogenous to the body. Thus, over time, the filling material disappears along with the contrast medium. As one of ordinary skill in the art will recognize, examination of the treatment site days to months after treatment will reveal less and less of an image as endogenous compounds replace the filing material (and the contrast medium). By analyzing the intensity changes at the treatment site, a physician can monitor the degree of healing of the aneurysm.

Another advantage of using glycosaminoglycans or mucopolysaccharides is that these large molecules show extremely little variation species to species. Therefore, human glycosaminoglycans are almost identical to avian glycosaminoglycans allowing the use of the avian glycosaminoglycan or mucopolysaccharide in treating a human patient without substantial risk of a foreign body reaction in the human patient. In fact, most medical grade glycosaminoglycans or mucopolysaccharides are produced from sources other than human sources and may contain residual proteins or other materials from those sources.

Once the aneurysm is filled, the hydrodynamics of the blood near the aneurysm become less abnormal. Subsequently, the filling material begins to break down and thrombin, blood cell decomposition products, blood protein components, other endogenous materials, and, in the case of aneurysms also treated with a coil, the decomposition products of the coil or any coil coating all begin to take the place of the filling material. For purposes of this disclosure, coil decomposition products are materials that were once part of a medical device that was inserted into an aneurysm. In some cases, the device was a wire coil, hence the term coil decomposition products. Coil composition products need not come from wire coils, but are the decomposition products from any medical device, as discussed above.

For purposes of this disclosure, an aneurytic site is a region in mammalian vasculature near an aneurysm or near aneurytic tissue. And for purposes of this disclosure, aneurytic tissue is any type of tissue associated with or created by the formation of an aneurysm or any tissue composing an aneurysm or the vascular tissue near an aneurysm.

Filling Material

Various compositions are suitable for applying or supplying to or into an aneurysm to treat it. The filling material of the current invention comprises a base (Component I) and optionally a contrast agent or medium (Component II) and optionally a drug or bioactive agent (component III). Of course, other materials and formulations for use on mammalian patients may also compose the filling material. One such material is a physiological buffer.

In some embodiments, an invention composition comprises a mixture of the Component I and Component II compositions. For purposes of this disclosure, an invention mixture is a combination of two or more components in which the components substantially retain their chemical identity upon combination. The components substantially retain the chemical nature that they had before combination into the mixture.

Component I

In some embodiments, the base comprises a glycosaminoglycan or a mucopolysaccharide. Useful glycosaminoglycans or mucopolysaccharides include hyaluronic acid, sodium hyaluronate, chondroitin sulfate, dermatan sulfate, keratan sulfate, or heparin sulfate, in some embodiments. Also, useful polyanionic polysaccharides include carboxymethylcellulose, carboxymethylamylose and their derivatives. These are described more fully below. In some embodiments, the base comprises hyaluronic acid. In these or other embodiments, hyaluronic acid comprises HEALON (a product of Abbott Medical Optics). A variety of embodiments use such HEALON bases, which are described below in the discussion of U.S. Pat. Nos. 5,681,825; 6,086,597; and 6,271,216.

U.S. Pat. No. 5,681,825, issued October 1997, discloses examples of useful hyaluronic acid base materials. In some embodiments, the base is an aqueous solution of hyaluronic acid with an average molecular weight of 4 million to 12 million. In some of these embodiments, the zero shear viscosity of the base hyaluronic acid ranges from 1 thousand to 80 thousand Pas. Other embodiments include hyaluronic acid bases with an average molecular weight of 4.5 million to 8 million. In some of these embodiments, the zero shear viscosity of the material is 1 thousand to 9 thousand Pas.

U.S. Pat. No. 6,086,597, issued in July 2000, also discloses examples of useful hyaluronic acid base materials. In some embodiments, the base is an aqueous solution of 18-40 mg sodium hyaluronate per milliliter of water in which the sodium hyaluronate has a $<M>_{r,M}=1\times10^6$ to $10\times10^6$. In some embodiments, the base is an aqueous solution of 20 mg of $<M>_{r,M}=3\times10^6$ sodium hyaluronate; 8.5 milligrams of sodium chloride, and one milliliter of water. In some embodiments, the base is an aqueous solution of 25 mg of $<M>_{r,M}=3\times10^6$ sodium hyaluronate; 8.5 milligrams of sodium chloride, and one milliliter of water.

U.S. Pat. No. 6,271,216, issued in August 2001, also discloses examples of useful hyaluronic acid base materials. In some embodiments, the base is an aqueous solution of about 0.1 to five percent by weight or one to three percent by weight sodium hyaluronate having an average molecular weight of $0.2\times10^6$ to $10.0\times10^6$ or $0.25\times10^6$ to $4\times10^6$. These solutions have sodium ions present from about 80 to 185 millimolar or 90 to 110 millimolar exclusive of the sodium contributed by the sodium hyaluronate. In some embodiments, the solution is prepared with 30 milligrams of sodium hyaluronate; 3-3.4 milligrams sodium chloride; and one milliliter of water. In some embodiments, the solution is prepared with 30 milligrams sodium hyaluronate, 4.3-4.7 milligrams sodium chloride, and one milliliter of water. In some embodiments, solutions prepared with 30 milligrams sodium hyaluronate, 3.2 milligrams sodium chloride, and one milliliter of water are useful. In some of these embodiments, the sodium hyaluronate has an average molecular weight of 400 thousand. Finally, as disclosed in the '216 patent, solutions prepared with 30 milligrams of sodium hyaluronate with a molecular weight of 400 thousand; 4.58 milligrams of sodium chloride, and one milliliter of water are useful in some embodiments as part of Component I. Some embodiments employ cross-linked hyaluronic acid as part of the base, as well. One type of cross-linked hyaluronic acid has disulfide cross-links.

In addition to polyanionic polysaccharides and hyaluronic-acid-based polymers, modified polymers may be used in the present invention. These are disclosed in U.S. Pat. No. 7,829, 118. Such polymers include polyanionic polysaccharides that have been modified in a number of ways. In some embodiments, the unmodified polyanionic polysaccharides are any one or any combination of hyaluronic acid, carboxymethylcellulose, carboxymethylamylose, chondroitin-4-sulfate, chondroitin-6-sulfate, dermatan sulfate, dermatin-6-sulfate, heparin sulfate, heparin, keratin sulfate and their derivatives.

Similar other useful polymers are known in the art, and described, for example, in U.S. Pat. No. 6,056,970. Other biodegradable polymers include fibrin, fibrinogen, starch, poly(amino acids); peptides, proteins, gelatin and collagen.

Hyaluronic acid may be derivatized by reacting its hydroxyl groups with divinyl sulfone. The hyaluronic acid will typically have a degree of modification of reactive hydroxyl groups ranging from 1 to 80%; 1 to 50%; or 1 to 25%. That is to say, a 1% degree of modification or substitution means that an average of 1% of the hyaluronic acid disaccharide units contain a vinyl sulfone group.

Alternatively, the polymer may be thiol-derivatized, such as a thiol-derivatized hyaluronic acid. Exemplary thiol-derivatized hyaluronic acid polymers include those described in U.S. Pat. Nos. 6,884,788; 6,620,927; 6,548,081, 6,537,979; 6,013,679; 5,502,081; and 5,356,883, relevant portions of which related to such thiol-derivatized polymers being incorporated herein by reference in their entireties.

Additional examples of hyaluronic acid polymers include cysteine-derivatized hyaluronic acid, including those polymers disclosed in "Controlled Release from Glycosaminoglycan Drug Complexes" R. V. Sparer et al.

Some embodiments use a gel comprised of the reaction product of two components. In those embodiments that employ such a filling material base, the gel's components must be chosen so that the material sets up relatively quickly—less than 60, 45, 30, 15, 5, or 1 seconds. Within that time, the material should exceed 80, 85, 90, or 95% of its final viscosity or modulus. For example, a gel based on silk elastin materials may be used as a component of the filling material.

Various embodiments use a Component I that has one or more of the following features: a non-particulate nature; a flowable nature; or a non-fibrotic nature. For purposes of this disclosure, having a non-particulate nature means that neither the glycosaminoglycan nor the mucopolysaccharide of Component I has been subjected to any physical or chemical treatment designed to make it take the form of a particle. For purposes of this disclosure, having a flowable nature means that the glycosaminoglycan or mucopolysaccharide of Component I can flow within a delivery device. For purposes of this disclosure, having a non-fibrotic nature means that the glycosaminoglycan or mucopolysaccharide of Component I does not produce enough fibrotic tissue to produce a permanent or obstructive scar in the vasculature.

A non-thrombogenic material is any material that, when inserted into mammalian vasculature, does not have a tendency to produce a blood clot substantially higher than the tendency of vascular tissue to produce a blood clot, when measured over a 1-hour, 2-hour, 1-day, 2-day, 1-week, or 2-week time.

For purposes of this disclosure, a high viscosity material is a material with a viscosity greater than or equal to that of mammalian blood, with a viscosity sufficiently high to prevent substantial mixing between the material and blood for 1-1000; 2-100; 2-50; 2-25; or 2-10 minutes, with a viscosity sufficiently high to allow the material to remain on aneurytic tissue or within an aneurysm for 1-1000; 2-100; 2-50; 2-25; or 2-10 minutes, or with a viscosity sufficiently high to allow the material to remain on aneurytic tissue or within an aneurysm long enough for the material to gel, harden, or solidify.

Component II

The base material may comprise any of the Component I materials described above, or the base material may comprise any combination of the Component I materials described above. Moreover, the base material may contain any other material that does not interfere with the function or operation of the base material so much that one of ordinary skill in the art would reject adding that other material. Some of those other materials are described below under the Component II and Component III headings.

Another optional component is a contrast medium for reasons described above or for other reasons. Useful contrast media include materials comprising metrizamide, iodecimol, ioglucol, ioglucamide, ioglunide, iogulamide, iomeprol, iopentol, iopromide, iosarcol, iosimide, iotasul, ioxilan, iohexyl, ioversol, iopamidol, iotrolan, ioxaglate, iodixanol, iothalamate, ioxithalamate, iodamide, metrizoate, copper-zinc ferrite, nickel-zinc ferrite, manganese-zinc ferrite, zinc ferrite, magnesium ferrite, α-ferric oxide, ferrosoferric oxide, diatrizoate, barium sulfate, diatrizoic acid, metrizoic acid, iotalamic acid, ioxitalamic acid, ioglicic acid, acetrizoic acid, iocarmic acid, methiodal, diodone, ioxaglic acid, iobitridol, iodoxamic acid, iotroxic acid, ioglycamic acid, adipiodone, iobenzamic acid, iopanoic acid, iocetamic acid, sodium iopodate, tyropanoic acid, calcium iopodate, ethyl esters of iodized fatty acids, iopydol, propyliodone, iofendylate, or lipiodol.

For purposes of this disclosure, a sufficient amount of a material comprising contrast media means that the material comprises enough contrast media to make the mixture medically imageable. For purposes of this disclosure, medically imageable means that the material is visible enough when imaged with a radiological device that the person treating the patient is able to detect that the mixture is entering the vasculature and to what extent the mixture is entering the vasculature in substantially real time. For purposes of this disclosure, a radiological device is any device capable of viewing inside a patient's body non-invasively, irrespective of whether or not the device employs electromagnetic radiation as part of the viewing process.

Other optional components in the filling material are drugs such as pro-healing drugs or growth factors. In some embodiments, an optional drug component is any pro-healing drug or growth factor or any combination of pro-healing drugs or growth factors.

As used herein, "pro-healing" refers to a moiety that aids in the healing process at the aneurysm or within the aneurysm. Pro-healing drugs are useful as drugs and are optionally added to the filling material. In some embodiments, prohealing drugs are materials that promote the controlled proliferation of muscle cells with a normal and physiologically benign composition, useful pro-healing drugs include enzymes, anti-inflammatory agents, antivirals, anticancer drugs, anticoagulant agents, free radical scavengers, steroidal anti-inflammatory agents, non-steroidal anti-inflammatory agents, antibiotics, estradiol, VEGF, an EPC antibody, biorest, nitric oxide donors, super oxide dismutases, endothelial progenitor cells, super oxide dismutases mimics, nitric oxide, 4-amino-2,2,6,6-tetramethylpiperidine-1-oxyl (4-amino-TEMPO), dexamethasone, clobetasol, aspirin, pro-drugs of these drugs, co-drugs of these drugs. Any compatible combination of pro-healing drug is also suitable for use in this invention.

The polypeptide Arg-Gly-Asp (RGD) has been demonstrated to be a bioactive factor for human endothelial cell attachment and therefore is expected to exhibit prohealing characteristics. In addition to RGD itself, cyclic RGD (cRGD) and RGD mimetics and small molecules capable of binding as does RGD to other adhesion receptors are within the scope of optional filling material components. RGD mimetics can be prepared by modification of RGD or cRGD. Peptide synthesis, including the synthesis of peptide mimetics, is well documented and can be readily achieved using, for example, combinatorial chemistry. Some examples of cRGD or RGD mimetics include V3 antagonists such as IIb/IIIb antagonists, one example of which is Abciximax; XJ 735; anti-3-integrin antibody F11; cRGD; and other sequences such as laminin-derived SIKVAV; laminin-derived YIGSR; KQAGDV; and VAPG.

Useful drugs also include any substance or combination of substances capable of exerting a therapeutic or prophylactic effect in the practice of the present invention as well as having positive pharmacological effects on the expression of the extracellular matrix. The active ingredient can also enhance wound healing in a vascular site or improve the structural and elastic properties of the vascular site.

Growth factors are also useful drugs in this invention. Growth factors include any one or any combination of vasoendothelial growth factor, fibroblast growth factor, hypoxia inducing factor, monocyte chemoattractant protein, lipid factors, vascular endothelial growth factors, fibroblast growth factors, nicotine, platelet derived growth factor, insulin-like growth factor 1, transforming growth factor, hepatocyte growth factor, estrogens, follistatin, proliferin, prostaglandin E1, prostaglandin E2, tumor necrosis factor, interleukin-8, hematopoietic growth factors, erythropoietin, granulocyte-colony stimulating factors, and platelet-derived endothelial growth factor.

Angiogenic substances are growth factors and may be any one or any combination of the following substances, and hormones and genes that encode any one of the following substances: vascular endothelial growth factor, fibroblast growth factors, monocyte chemoattractant proteins, transforming growth factor beta, transforming growth factor alpha, lipid factors, hypoxia-inducible factor 1-alpha, PR39, nicotine, insulin-like growth factors, placental growth factor, hepatocyte growth factor, estrogen, follistatin, proliferin, cytokines, tumor necrosis factor, erythropoietin, granulocyte colony-stimulating factor, granulocyte macrophage colony-stimulating factor, and angiogenin.

Also, endogenous compounds may be added to these compounds as drugs, see below.

Anti-inflammatory agents may be added to the filling material mixture. Suitable anti-inflammatory agents include, without limitation, steroidal anti-inflammatory agents, a nonsteroidal anti-inflammatory agent, or a combination thereof. In some embodiments, anti-inflammatory agents include clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, morniflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. The anti-inflammatory agent may also be a biological inhibitor of pro-inflammatory signaling molecules including antibodies to such biological inflammatory signaling molecules.

Depending on their source, the components may contain trace amounts of extraneous, but supposedly benign materials. Thus, the compositions of this invention may comprise one or more of these trace materials. For example, an avian-sourced glycosaminoglycan or mucopolysaccharide may contain trace amounts of avian protein, which in turn leads to inventive embodiments that may comprise avian protein.

In some embodiments, the filling materials or components of the filling materials are prepared to be hydrogels.

For purposes of this document, filling materials assembled or produced outside of the patient are referred to as stage I materials. After a stage I material is delivered to the aneurysm, the patient's body begins to break the material down. Moreover, during this time, blood cells and proteins migrate into the stage I material creating a new material within the aneurysm—called a stage II material. The stage II material, formed in situ, is suitable for filling aneurysms. Thus, a stage II material may comprise any of the components of the stage I material, may comprise blood cells or blood proteins, may comprise glycosaminoglycan or mucopolysaccharide decomposition products, may comprise blood cell or blood protein decomposition products, may comprise other endogenous materials or may comprise, for those embodiments employing some type of coil, materials arising from the coil's decomposition.

Endogenous materials include those materials created by the patient's body that one of ordinary skill in the art would expect the patient's body to create or deposit near the aneurysm treatment site. Specifically, endogenous compounds include among other compounds, extracellular matrix. The extracellular matrix is the extracellular part of animal tissue that usually provides structural support to the animal cells in addition to performing various other important functions. The extracellular matrix is the defining feature of connective tissue in animals. Extracellular matrix includes the interstitial matrix and the basement membrane. Interstitial matrix is present between various animal cells (i.e., in the intercellular spaces). Gels of polysaccharides and fibrous proteins fill the interstitial space and act as a compression buffer against the stress placed on the matrix. The extracellular matrix is composed of an interlocking mesh of fibrous proteins and glycosaminoglycans (GAGs). GAGs are carbohydrate polymers and are usually attached to extracellular matrix proteins to form proteoglycans. Heparan sulfate is a linear polysaccharide found in all animal tissues. Chondroitin sulfate is a sulfated glycosaminoglycan composed of a chain of alternating sugars. Keratan sulfate, also called keratosulfate, is any of several sulfated glycosaminoglycans that have been found especially in the cornea, cartilage, and bone. Collagen is a group of naturally occurring proteins. In nature, it is found exclusively in animals, especially in the flesh and connective tissues of mammals. It is the main component of connective tissue, and is the most abundant protein in mammals, making up about 25% to 35% of the whole-body protein content. Collagen, in the form of elongated fibrils, is mostly found in fibrous tissues such as tendon, ligament and skin, and is also abundant in cornea, cartilage, bone, blood vessels, the gut, and intervertebral disc. Elastin is a protein in connective tissue that is elastic and allows many tissues in the body to resume their shape after stretching or contracting. Elastin helps skin to return to its original position when it is poked or pinched. Fibronectins are proteins that connect cells with collagen fibers in the extracellular matrix. Laminins are major proteins in the basal lamina, a protein network foundation for most cells and organs. Generally see Extracellular Matrix article on Wikipedia.org.

The difference between the extracellular matrix materials described here as endogenous compounds and those described above as Component I constituents is that the endogenous compounds are prepared by the patient's body and become involved with the aneurysm because of the treatment of the aneurysm. The ones described above, although of similar or perhaps nearly identical structure are typically produced synthetically or by another organism. But this need not be the case.

In some embodiments, the stage I material decomposes and eventually substantially completely decomposes. In some of these embodiments, the stage I material substantially completely decomposes after 7-90 days.

Delivery

The practitioner can deliver the filling material percutaneously using a catheter system, a balloon catheter system, or a needle catheter system. Alternatively, the practitioner can deliver the material directly to the aneurysm by hypodermic needle injection or by some surgical techniques such as open surgery or laparoscopic surgery.

Some embodiments comprise a treatment method wherein an aneurysm is visualized such as by fluoroscopy. A catheter or other delivery devices is inserted into the patient percutaneously and tracked along the vasculature until the delivery device is positioned near the aneurysm. One way of doing this is tracking a catheter over a guidewire. Once the delivery device is correctly positioned near the aneurysm, a filling material is delivered to the aneurysm. Some embodiments of the filling material comprise a glycosaminoglycan and, optionally, a contrast media, a physiological buffer or both. In these or other embodiments, the filling material comprises a glycosaminoglycan selected from hyaluronic acid, sodium hyaluronate, chondroitin sulfate, dermatan sulfate, keratan sulfate, or heparin sulfate; and optionally a contrast media, a physiological buffer, or both. In these or other embodiments, the contrast media is selected from material comprising metrizamide, iodecimol, ioglucol, ioglucamide, ioglunide, iogulamide, iomeprol, iopentol, iopromide, iosarcol, iosimide, iotasul, ioxilan, iohexyl, ioversol, iopamidol, iotrolan, ioxaglate, iodixanol, iothalamate, ioxithalamate, iodamide, metrizoate, copper-zinc ferrite, nickel-zinc ferrite, manganese-zinc ferrite, zinc ferrite, magnesium ferrite, α-ferric oxide, ferrosoferric oxide, diatrizoate, barium sulfate, diatrizoic acid, metrizoic acid, iotalamic acid, ioxitalamic acid, ioglicic acid, acetrizoic acid, iocarmic acid, methiodal, diodone, ioxaglic acid, iobitridol, iodoxamic acid, iotroxic acid, ioglycamic acid, adipiodone, iobenzamic acid, iopanoic acid, iocetamic acid, sodium iopodate, tyropanoic acid, calcium iopodate, ethyl esters of iodized fatty acids, iopydol, propyliodone, iofendylate, or lipiodol.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

Finally, headings are for the convenience of the reader and do not alter the meaning or content of the disclosure or the scope of the claims.

What is claimed is:

1. A method of treating an aneurysm in a patient in need thereof, comprising:
    positioning a catheter percutaneously near an unsealed aneurysm in a vasculature of a patient;
    flowing a non-particulate, non-fibrotic aneurysm filling material through the catheter, wherein the non-particulate, non-fibrotic aneurysm filling material consists of:
        a glycosaminoglycan selected from a group consisting of hyaluronic acid, sodium hyaluronate, chondroitin sulfate, dermatan sulfate, and keratan sulfate, and
        a contrast media imageable by fluoroscopy;
    depositing the non-particulate, non-fibrotic aneurysm filling material from the catheter into the unsealed aneurysm in the vasculature, wherein the non-particulate, non-fibrotic aneurysm filling material is deposited onto an aneurytic tissue within the unsealed aneurysm; and
    imaging the non-particulate, non-fibrotic aneurysm filling material within the aneurysm by fluoroscopy;
    wherein the non-particulate, non-fibrotic aneurysm filling material includes a viscosity such that the non-particulate, non-fibrotic aneurysm filling material remains in the unsealed aneurysm, and wherein the non-particulate, non-fibrotic aneurysm filling material does not induce a fibrotic response that permanently scars the vasculature when the non-particulate, non-fibrotic aneurysm filling material is in the aneurysm.

2. The method of claim 1, wherein the contrast media is selected from metrizamide, iodecimol, ioglucol, ioglucamide, ioglunide, iogulamide, iomeprol, iopentol, iopromide, iosarcol, iosimide, iotasul, ioxilan, iohexyl, ioversol, iopamidol, iotrolan, ioxaglate, iodixanol, iothalamate, ioxithalamate, iodamide, metrizoate, copper-zinc ferrite, nickel-zinc ferrite, manganese-zinc ferrite, zinc ferrite, magnesium ferrite, α-ferric oxide, ferrosoferric oxide, diatrizoate, barium sulfate, diatrizoic acid, metrizoic acid, iotalamic acid, ioxitalamic acid, ioglicic acid, acetrizoic acid, iocarmic acid, methiodal, diodone, ioxaglic acid, iobitridol, iodoxamic acid, iotroxic acid, ioglycamic acid, adipiodone, iobenzamic acid, iopanoic acid, iocetamic acid, sodium iopodate, tyropanoic acid, calcium iopodate, ethyl esters of iodized fatty acids, iopydol, propyliodone, iofendylate, or lipiodol, and wherein the glycosaminoglycan or mucopolysaccharide is selected from hyaluronic acid, sodium hyaluronate, chondroitin sulfate, dematan sulfate, or keratan sulfate.

3. The method of claim 1, wherein depositing the non-particulate, non-fibrotic aneurysm filling material into the unsealed aneurysm comprises inserting a needle into the unsealed aneurysm at an aneurytic site or delivering the catheter or a needle catheter delivery system device to the aneurytic site.

4. The method of claim 3 further comprising delivering a coil to the aneurysm before, during, or after depositing the non-particulate, non-fibrotic aneurysm filling material.

5. The method of claim 2, wherein depositing the non-particulate, non-fibrotic aneurysm filling material into the unsealed aneurysm comprises inserting a needle into the unsealed aneurysm at an aneurysm site or delivering the catheter or a needle catheter delivery system device to the aneurytic site.

6. The method of claim 5 further comprising delivering a coil to the aneurysm before, during, or after depositing the non-particulate, non-fibrotic aneurysm filling material.

7. The method of claim 4, wherein the glycosaminoglycan includes a zero-shear viscosity greater than about 1,000 Pa-s at a first molecular weight.

8. The method of claim 7, wherein the contrast media includes a second molecular weight in a ratio to the first molecular weight ranging from about 1:1.2 to 1:1,000,000.

9. The method of claim 8, wherein the contrast media is iodinated such that the non-particulate, non-fibrotic aneurysm filling material is medically imageable by fluoroscopy.

10. The method of claim 9, wherein the non-particulate, non-fibrotic aneurysm filling material has a hydrogel nature and breaks down within the aneurysm over 7 to 90 days.

11. The method of claim 6, wherein the glycosaminoglycan includes a zero-shear viscosity greater than about 1,000 Pa-s at a first molecular weight.

12. The method of claim 11, wherein the contrast media includes a second molecular weight in a ratio to the first molecular weight ranging from about 1:1.2 to 1:1,000,000.

13. The method of claim 12, wherein the contrast media is iodinated such that the non-particulate, non-fibrotic aneurysm filling material is medically imageable by fluoroscopy.

14. The method of claim 13, wherein the non-particulate, non-fibrotic aneurysm filling material has a hydrogel nature and breaks down within the aneurysm over 7 to 90 days.

* * * * *